United States Patent
Mischler et al.

(10) Patent No.: US 8,160,665 B2
(45) Date of Patent: Apr. 17, 2012

(54) MICRONEEDLE ARRAYS WITH ATR SENSOR

(75) Inventors: Reinhold Mischler, Ludwigshafen (DE); Gerhard Werner, Weinheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1432 days.

(21) Appl. No.: 11/675,725

(22) Filed: Feb. 16, 2007

(65) Prior Publication Data
US 2007/0191696 A1 Aug. 16, 2007

(30) Foreign Application Priority Data

Feb. 16, 2006 (EP) ..................................... 06003127

(51) Int. Cl.
*A61B 5/1455* (2006.01)
(52) U.S. Cl. ......... 600/310; 600/316; 600/322; 600/347
(58) Field of Classification Search .................. 600/316, 600/317, 322, 326, 327, 310, 347, 373, 573, 600/576; 604/317
See application file for complete search history.

(56) References Cited

U.S. PATENT DOCUMENTS

| | | | |
|---|---|---|---|
| 4,169,676 A | 10/1979 | Kaiser | |
| 5,179,951 A * | 1/1993 | Knudson | 600/310 |
| 5,801,057 A | 9/1998 | Smart et al. | |
| 6,128,091 A * | 10/2000 | Uchida et al. | 356/432 |
| 6,169,915 B1 * | 1/2001 | Krumbiegel et al. | 600/372 |
| 6,312,612 B1 | 11/2001 | Sherman et al. | |
| 6,424,851 B1 | 7/2002 | Berman et al. | |
| 6,507,396 B1 * | 1/2003 | Godfried et al. | 356/300 |
| 6,603,987 B2 | 8/2003 | Whitson | |
| 7,039,447 B2 | 5/2006 | Berman et al. | |
| 2002/0185384 A1 | 12/2002 | Leong et al. | |
| 2003/0135161 A1 | 7/2003 | Fleming et al. | |
| 2003/0208113 A1 * | 11/2003 | Mault et al. | 600/316 |
| 2004/0217018 A1 | 11/2004 | Leong et al. | |
| 2006/0043301 A1 | 3/2006 | Mantele et al. | |

FOREIGN PATENT DOCUMENTS

| | | |
|---|---|---|
| JP | 2005-530986 A | 10/2005 |
| JP | 2006-521555 A | 9/2006 |
| JP | 2007-532260 A | 11/2007 |
| WO | WO00/35530 | 6/2000 |

(Continued)

OTHER PUBLICATIONS

Mendelson et al. "Blood glucose measurements by multiple attenuated total reflection and Infrared absorption spectroscopy" IEEE Transactions on Biomedical Engineering, vol. 37, No. 5, pp. 458-465, May 1990.*

(Continued)

*Primary Examiner* — Eric Winakur
*Assistant Examiner* — Chu Chuan (JJ) Liu
(74) *Attorney, Agent, or Firm* — Bose McKinney & Evans LLP

(57) ABSTRACT

A sensor is described for optically determining the concentration of an analyte in a body fluid. This sensor comprises a needle arrangement which has at least one hollow needle having a hollow space extending from the distal end to the proximal end, the distal end of which is suitable for lancing. The proximal end of the needle opens into a chamber in which liquid that enters through the distal end of the needle can be collected. A window which is at least partially permeable to infrared radiation is in direct contact with the chamber.

50 Claims, 5 Drawing Sheets

FOREIGN PATENT DOCUMENTS

| | | |
|---|---|---|
| WO | WO 03/083458 A2 | 10/2003 |
| WO | WO 2004/085995 A2 | 10/2004 |
| WO | WO 2005/103678 A2 | 11/2005 |

OTHER PUBLICATIONS

Malchoff, C.D., et al., A Novel Noninvasive Blood Glucose Monitor, Diabetes Care, 2002, vol. 25, No. 12.

Heise, H.M.. et al., Investigation of Exerimental Errors in the Quantitative Analysis of Glucose in Human Blood Plasma by ATR-IR Spectroscopy, Journal of Molecular Structure, 1995, vol. 348, pp. 21-24.

Bittner, A., Heise, H.M., Koschinsky, TH, Gries, F.A., "Evaluation of Microdialysis and FT-IR ATR-spectroscopy for in-vivo Blood Glucose Monitoring," Mikrochim. Acta [Suppl.] 14, 827-828 (1997).

Heise, .M., Bittner, A., Koschinsky, T., Gries, F.A., "Ex-vivo determination of blood glucose by microdialysis in combination with infrared attenuated total reflection spectroscopy," Fresenius J Anal Chem (1997) 259: 83-87.

Zahn, J.D., Trebotich, D., Liepmann, D., "Microdialysis Microneedles for Continuous Medical Monitoring," Biomedical Microdevices 7: 1, 59-69, 2005.

US 6,230,044, 05/2001, Afanassieva, of al. (withdrawn)

* cited by examiner

MICRONEEDLE ARRAYS WITH ATR SENSOR

RELATED APPLICATIONS

This application claims priority to EP 06003127.5, filed Feb. 16, 2006, the entire disclosure of which is hereby incorporated herein by reference.

BACKGROUND

The invention relates to the field of diagnostics and in particular to a painless collection of fluid for optical measurement of blood components. There are a variety of analytical systems for detecting analytes such as glucose, in which blood is collected from the patient and applied to a test carrier in order to then be measured in a measuring instrument separately from the blood collection. These measuring instruments may utilize optical detection as well as electrochemical detection. These systems in most cases have a test strip on which the patient must deposit a drop of blood.

A combination is described in U.S. Pat. No. 6,603,987 in which a needle array is used which is connected with a test strip. A disadvantage of this method is that it cannot be used for continuous measurement since the test strip can only be used for a single measurement. This means that the patient must prick himself several times daily with the needle array.

U.S. patent application number US 20030185384 describes the production of microneedles and the linkage of a needle array with a sensor element. An electrochemical detection element is disclosed which is connected to the needle array by means of a transfer medium (for example a hydrophilic porous material which takes up the liquid). This system also has the disadvantage that it cannot be used to continuously monitor the patient. This again leads to the disadvantage for the patient that he must prick himself several times daily.

As a result of the reagents used for the analysis as they are described in the prior art, the test element can only be used for one measurement since the reagents are consumed in the reaction with the analyte. This means that the patient has to exchange the test element for a new one after each measurement. In addition to the work required by the patient to change the test elements, another disadvantage is that the system can only be miniaturized to a limited extent if the system is to remain manageable for the patient.

SUMMARY OF THE INVENTION

The present invention addresses the disadvantages noted above and provides a miniaturized analytical system which can continuously analyze body fluid of the patient. A needle arrangement is provided which has at least one needle whose distal end is suitable for lancing and whose proximal end opens into a chamber. An array of needles is used in an exemplary embodiment. This needle array can include two to several hundred needles. The needles can be arranged in a row or in a two-dimensional matrix, and the arrangement of needles can be randomized. The array can have an angular or round design.

An exemplary form of needle arrangement is an elongate, rectangular arrangement. This needle arrangement is combined with a window which is at least partially permeable to infrared radiation. The chamber forms an interspace between the needle arrangement and window. Hence, radiation guided through the window can interact with the liquid in the chamber. The needles of the needle arrangement are hollow in this embodiment and the proximal end of the hollow space of the needles opens into the chamber. The window is arranged opposite the proximal ends of the needles. The window is permeable to light in at least part of the wavelength range of 500-20,000 nm. An exemplary wavelength range is from 2000-12,000 nm. The path length of the window can be about 0.5 mm. In a particular embodiment, the path length can be 0.025-0.2 mm. The volume of the chamber can be between 10 and 1000 nl depending on the number of needles and geometry of the chamber. The needles can be joined together by bars. The tips of the needles are shaped such that they penetrate the skin only to such an extent that interstitial fluid is preferentially collected. This means that the needle tips have a length of only a few 100 μm up to 1 mm. The needles have a hollow space through which the body fluid enters the chamber. A filter membrane may be located between the location the needle cavity opens into the chamber and the chamber space. This membrane prevents large proteins from entering the chamber and can be made from polymers or silicon.

The chamber, which is closed by the window, is located on the opposite side of the membrane. This window preferably consists of materials that are permeable to infrared radiation, such as silver, silver halogenides, zinc selenide, diamond, germanium or silicon. If diamond is not used as the main material, it is possible to coat the window material with diamond. This prevents attachment of proteins to the window surface, which can undesirably attenuate the signal. The window may take various geometries. The needle array may have a different geometry and dimension than the window. Thus, it is possible to combine a round needle array with an angular window. One exemplary embodiment is a rectangular window which extends over needles arranged in one or two or more rows. An exemplary size of this array is 0.01 to 25 $mm^2$, more particularly, in the size range of 0.01 to 0.25 $mm^2$.

A radiation source (e.g. a thermal infrared radiation source such as a thin film radiator) is located at one end of the window. A detector may be located on the opposite side of the radiator at the other end of the window, such as a pyroelectric detector array with interference filters. The radiation which is irradiated by the radiation source into the window is preferably monochromatic. This radiation is used to build up an evanescent field at the sides of the window which interacts with the liquid in the chamber. If monochromatic radiation is used, interaction takes place only with very particular molecular configurations. This ensures that only those molecules are detected which have certain molecular groups, such as glucose molecules. This interaction leads to an attenuation of the light energy. This energy absorption or light absorption is determined with the aid of the detector. There is a direct correlation between the amount of absorbed radiation and the analyte concentration. The concentration of the analyte can be determined on the basis of this correlation. The use of light attenuation by an evanescent field for analyte determination is known among others under the name of ATR (attenuated total reflection) (A. Bittner et al., Microchim. Acta [Suppl.] 14, 827-828 (1997)) and reference is made to this citation.

In an exemplary embodiment, the analytical system is applied to the skin of the patient by means of an adhesive medium. This adhesive medium can, for example, be a plaster into which the analytical system is integrated. The needle tips of the needle array are pressed into the skin by applying a little pressure to the plaster, and fluid can flow out of the skin into the chamber. In order to ensure energy supply and data transfer into this closed system, the radiation source as well as the detector can be selected such that they are mechanically uncoupled from control elements. Data transfer with a separate control and measuring instrument then takes place by means of electrical interfaces. Another possibility is to couple light guides to the window which, limits the potential for miniaturization.

An advantage of this sensor is that it has a long shelf-life and can be easily sterilized. This is due to purely optical detection without using chemicals with limited storage life and limited activity after sterilization. These factors do not have to be taken into consideration with the described sensor, and it is possible to sterilize the completely assembled sensor. Its shelf-life is not limited by sensitive reagents. Furthermore, an exemplary embodiment of the system includes a light source for coupling the radiation into the window, a detector for capturing the radiation at the opposite side of the window and for generating measurement signals, and an evaluation device for calculating the concentration of the analyte from the measurement signals. This system can be integrated into a plaster-like structure such that the needle tips of the needle array are pressed into the skin when the plaster is applied to the skin.

The system can have radiation sources as well as detectors which can be controlled and read by means of electrical interfaces such as infrared or radio interfaces. No further contacting of the electrical and optical units is necessary in such a system. The patient can move freely and the system is screened by the plaster from external mechanical influences. The alternative coupling of the radiation source or the detector by means of light guides results in a more voluminous and more open system which cannot be completely screened from mechanical influences.

Advantages of the sensor according to the invention are that it does not require reagents for analysing the sample. This enables a high integration of the components which in turn enables a ready miniaturization of the system. The sensor as well as the system can be easily handled by the patient, since apart from affixing the sensor to the skin, only a few handling steps are necessary. The sensor as well as the system can be easily sterilized and can be made to have a long shelf-life since no sensitive chemicals or reagents are required for the analysis. Risk of contaminating the patient with chemicals is low due to the omission of reagents.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

Corresponding reference numerals are used to indicate corresponding parts throughout the several views.

DETAILED DESCRIPTION

Figure 1:
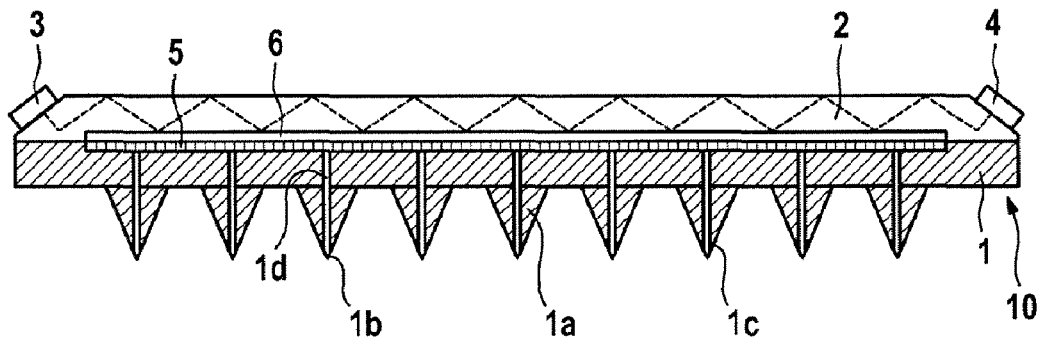
FIG. 1 is a schematic diagram of a needle array in accordance with an exemplary embodiment of the present invention shown in a side view.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

A sensor is described which is used to optically determine concentrations of an analyte in a liquid. In particular, this liquid consists of a body fluid such as blood, plasma, serum or interstitial fluid. It is collected by a needle array having at least one needle which penetrates into the skin of the patient.

Needle

This sensor comprises a needle array which has at least one hollow needle whose distal end is suitable for lancing and whose proximal end opens into a chamber into which liquid can enter. The needle tips can be, e.g., 100 μm to 1 mm in length. The diameter of the needle is preferably no more than 100 μm. In an exemplary embodiment, the diameter of the needles is between 20 and 70 μm. The needles have a hollow space through which the body fluid can pass and enter the chamber. In this connection, the inner diameter of the needle is between 10 and 60 μm, preferably between 15 and 40 μm. For this purpose, the needles are hollow inside. The liquid is, for example, collected from the skin of the patient by pressing at least one needle into the skin. The distal end of the needle is shaped such that it has a tip region, part of which extends over the length of the needle and in an exemplary embodiment extends up to the point where the needle discharges into the chamber. An alternative embodiment is a needle which has a capillary channel which adjoins the tip region and which extends over a part of the needle, and in an exemplary embodiment, extends over the entire length of the needle. A region of this capillary channel starting at the tip and extending beyond the tip is open towards the outside as described in patent publication no. US 200318282. The needles can be composed of various materials, such as metal, silicon, ceramic or polymer, such as polycarbonate. The needle is hollow over its length from its tip to where it joins the chamber.

Needle Array

Several such hollow needles can be arranged in a needle array. An exemplary embodiment contains between 10 and 100 needles in a two-dimensional matrix; but there can also be more or fewer needles. The rows can be arranged in lines next to one another. An exemplary arrangement of this array is a rectangle or square. Alternatively, the needles can also be arranged in a circle or oval. The needle array can have a different geometry and dimension than the window. Thus, a combination of a round needle array with an angular window is possible, as is the converse combination of an angular needle array with a round window. An exemplary embodiment, which is described in the following as being representative for all other arrangements of window and needle array, is a rectangular window which extends over the needles arranged in one or two or more rows. An exemplary size of this array is 0.01 to 25 mm$^2$, and a particular embodiment is in the size range of 0.01 to 0.25 mm$^2$.

Membrane

A membrane may be situated between the proximal ends of the needle or of the needle array and the chamber, which prevents large molecules (greater than about 10 TDa) from blocking the chamber or from depositing on the measuring surface of the window and thus causing interference. This membrane may be made from polymers, cellulose, silicon or polyamide (PA). It can also be a nuclear track-etched membrane composed of polycarbonate (PC). Nuclear track-etched membranes have a high mechanical and chemical stability. An exemplary embodiment of the membrane has a silicon layer or it consists of a silicon layer as described, for example, in the publication of Zahn et al. (Microdialysis Microneedles for continuous Medical Monitoring; Biom. Microdevices 7:1, 59-69, 2005). This membrane has very small dimensions and, moreover, it can be manufactured in a process together with the needles and, depending on the material, alternatively, also with the window.

Chamber and Volume Flow

The chamber which extends between the needle array and the window is used to bring at least part of the collected body fluid into contact with the window. The dimension of the chamber is selected such that an adequate wetting of the window can take place and also that a good exchange between body fluid and chamber fluid is ensured. Very different dimensions of the chamber can be selected depending on whether the liquid exchange between the chamber and skin occurs exclusively by means of diffusion or whether an artificial liquid flow is generated. In the case of exchange by means of diffusion, the volume of the chamber should be as small as possible so that there is no time delay between the measured concentration in the chamber and the current concentration in the skin. A volume range in which the time lag is only a few minutes is between 0.001 and 5 mm$^3$ including the volume of the needle cavities. An exemplary range is between 0.01 and 0.1 mm$^3$.

In an alternative embodiment of the sensor, a larger volume of the chamber can be selected because liquid is actively transported by the needle array into the chamber. This can, for example, be made possible by the selection of the materials for the window and its thickness. If the window is made of silicon and is not thicker than 0.025-0.2 mm, it can be made to oscillate in the longitudinal direction. The liquid can be moved in the chamber by means of this oscillating movement. This allows an active exchange of liquid between the chamber and body fluid in the skin of the patient. The oscillation of the window can for example be excited and controlled by a piezoelectric element. This piezo element can be attached to the outside of the window. Alternatively, the window can be oscillated by a mechanical transfer of force onto the thin window. In this case the choice of the material would not be limited to silicon.

Optics

A source of radiation is situated on at least one side of the window to couple (transmit) light into the window. This is preferably a side face of the window, which is predominantly parallel to the alignment of the needles. If the side faces have an unequal length it is particularly preferable to use a short side face to uncouple the light in order to have the longest possible optical path above the chamber. This allows an increase in the amount of irradiated light. Light can either be irradiated over the entire area of the window or light can be transmitted into the window by arranging at least one radiation source over at least one part of the area of the window.

Thus, at least one radiation source can either be glued onto the window or be mechanically coupled to the window by means of at least one light guide. If the radiation source and detector are not glued onto the window, an optomodule can be used to couple the radiation source or the detector. The detector and/or the radiation source can be integrated into the optomodule or be connected to the optomodule by means of a light guide. If the radiation source and detector are connected to the window by a light guide, the light guide which leads to the light source or the detector is connected to the window of the sensor by the optomodule. In so doing the optomodule ensures a planar coupling of the light guide to the window. It consists of a holder which is connected on one side to the light guide and on the other side to the window. The connection to the light guide as well as to the window is detachable. This connection can be a plug or screw connection or any other detachable connection. The optomodule can be configured such that it can couple to both light guides. In this manner an optical link can at the same time be made and detached again between the system and the optical modules, such as the light source and detector. This simplifies use for the patient since this process can be managed with one hand.

Window

The window preferably consists of materials that are permeable to infrared, such as silver, silver halogenides, zinc selenide, diamond, germanium or silicon. If diamond is not used as the main material, it is possible to coat the window material with diamond. This prevents undesirable attachment of proteins to the window surface, which can attenuate the signal. The window may have various geometries.

The coupling side of the window is ground to an ideal angle in order to perfectly transmit the light into the window. This angle is between 0° and 60°, preferably between 30° and 50°. This angle depends on the wavelength of the irradiated light since total reflection should be achieved in the window. The light is transmitted from the window for detection on another face of the window which is preferably the face opposite to the radiation source. Also, in this case there is an ideal angle between 0° and 60°, preferably between 30° and 50°. The detector can also be either glued on or be mechanically coupled to the window by means of a light guide.

Light Source/Detector

As already mentioned, monochromatic light as well as polychromatic light can be coupled or transmitted into the window. In the case of monochromatic irradiation into the window, a pyroelectric detector is, for example, used. The irradiation of monochromatic light can either be achieved by a monochromatic light source or by a polychromatic light source, in which case the light that is coupled into the window is limited by filters to certain wavelengths. In the case of polychromatic irradiation and detection, a pyroelectric detector array can, for example, be used, which is provided with various interference filters. In this manner it is possible to detect absorptions at various wavelengths and thus various molecular groups. An exemplary method of applying the filter and light source to the window is to coat suitable layers by evaporation. The use of monochromatic light enables molecules to be detected which have an atomic configuration that absorbs light exactly at this wavelength. Many different atomic configurations can be excited by using more than one wavelength to build up the evanescent field. The quantification of a molecule can be improved by correlating different wavelength ranges. In this manner it is possible to detect several molecular groups in parallel. Examples of different analytes that can be detected are glucose, cholesterol, creatinine, urea and triglycerides.

System

The sensor as described above for optically determining the concentration of an analyte in a liquid can also be used in a system. This system additionally comprises a light source to couple radiation into the window, a detector to capture the radiation at the opposite side of the window and to generate measurement signals. The system can additionally include an evaluation device to calculate the concentration of the analyte from the measurement signals.

In an exemplary embodiment, the light source as well as the detector are applied to one face of the window. They can either be glued or vapour-coated onto the window surface. In this case several layers of different materials are vapour-coated which are at least partially electrically conductive and can convert electrical energy into light.

In an alternative embodiment in which the light source and/or detector are not directly connected to the window, the system can additionally comprise an optomodule. This optomodule is used to couple light-conducting fibers to the window. This variant allows the use of conventional detectors and light sources but the handling of the system is less comfortable for the patient. The patient must carry out additional handling steps such as coupling the optomodule to the sensor. This alternative is very practical when the sensor or the system are only seldom connected to the optomodule which is particularly the case for short cycles of use. The system can thus not only be used for continuous measurement over relatively long time periods, but can also be used for a single measurement.

In the system the sensor can additionally be applied to the skin of the patient by an adhesive medium (e.g. a plaster). In this case the sensor is permanently connected to the adhesive medium. The at least one needle tip of the needle array is pressed into the skin by exerting a slight pressure on the adhesive medium and fluid can enter the chamber from the skin. In this case the radiation source as well as the detector can be selected such that they are mechanically uncoupled from control elements. Data transfer with a separate control and measuring instrument then takes place by means of electrical interfaces. Another possibility is to couple light guides to the window which limits the potential for miniaturization. The use of an optomodule is advantageous for this variant.

In an exemplary embodiment of the system, the sensor and an optomodule can be integrated in the form of a watch where at least one needle of the needle array is attached to the rear side of the watch face and can penetrate the skin of the patient when he wears the watch. The watch has an evaluation unit and a display for the evaluated measured data. The system can comprise an infrared interface with another system for registering the measured data.

A needle array in combination with a radiation window is shown in FIG. 1. The needle array 1 consists of a silicon hollow needle pad 1a. It is fluidly connected to the measuring chamber 6 via a membrane 5 to separate the high molecular weight components (above about 10,000 Daltons). A window 2 is located on the side of the measuring chamber 6 opposite the needle array 1. This window 2 extends over the entire length of the needle array 1. Needle 1a has a distal end 1c and a proximal end 1d. The opening of the needle 1b extends from the distal 1c to the proximal end 1d over the entire length of the needle 1a. The needles 1a can adopt a one-dimensional arrangement, i.e., be arranged in one row next to one another in which between two and 1000 needles can be situated in one row. However, an exemplary embodiment is for several such rows to be arranged next to one another. For example, 10 or more such rows can be arranged next to one another to form a two-dimensional matrix.

Figure 2:
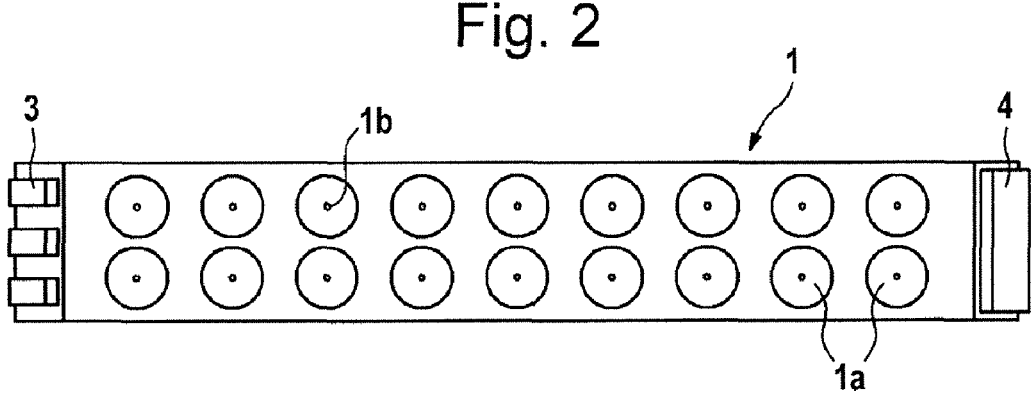
FIG. 2 is a top view of a needle array with a monochromatic radiation source and IR detector.
Figure 3:
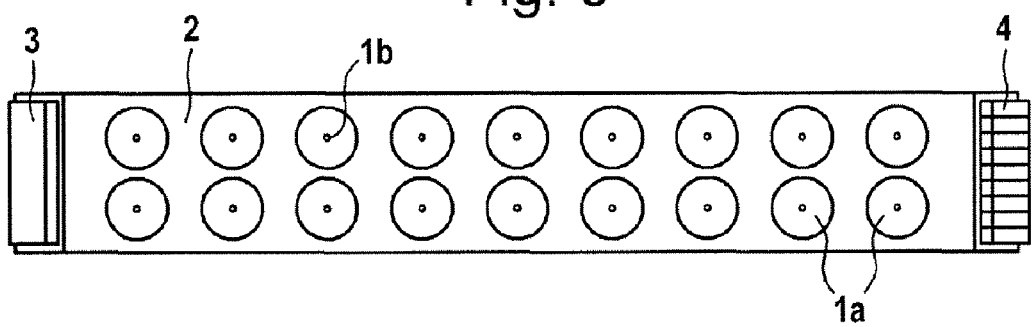
FIG. 3 is a top view of a needle array having a polychromatic radiation source and pyroelectric detector array.

FIG. 2 shows the needle array 1 in a top view. In this example two rows of needles 1a are shown but they could also be displaced relative to one another. A light source 3 is mounted on one side to the short sides of the window 2. This can for example be an infrared radiation source such as a quantum cascade laser (QCL); but it is also possible to use other monochromatic light sources. Alternatively, it is also possible to use non-monochromatic light sources. This is shown in FIG. 3. However, in this case an interference filter must be used between the light source (3) and window 2. The detector 4 is attached to the second short side of the window. When using a monochromatic light source this can, for example, be a pyroelectric detector as in FIG. 2. A pyroelectric detector array with interference filters is shown in FIG. 3 for detecting various wavelengths.

Figure 4:
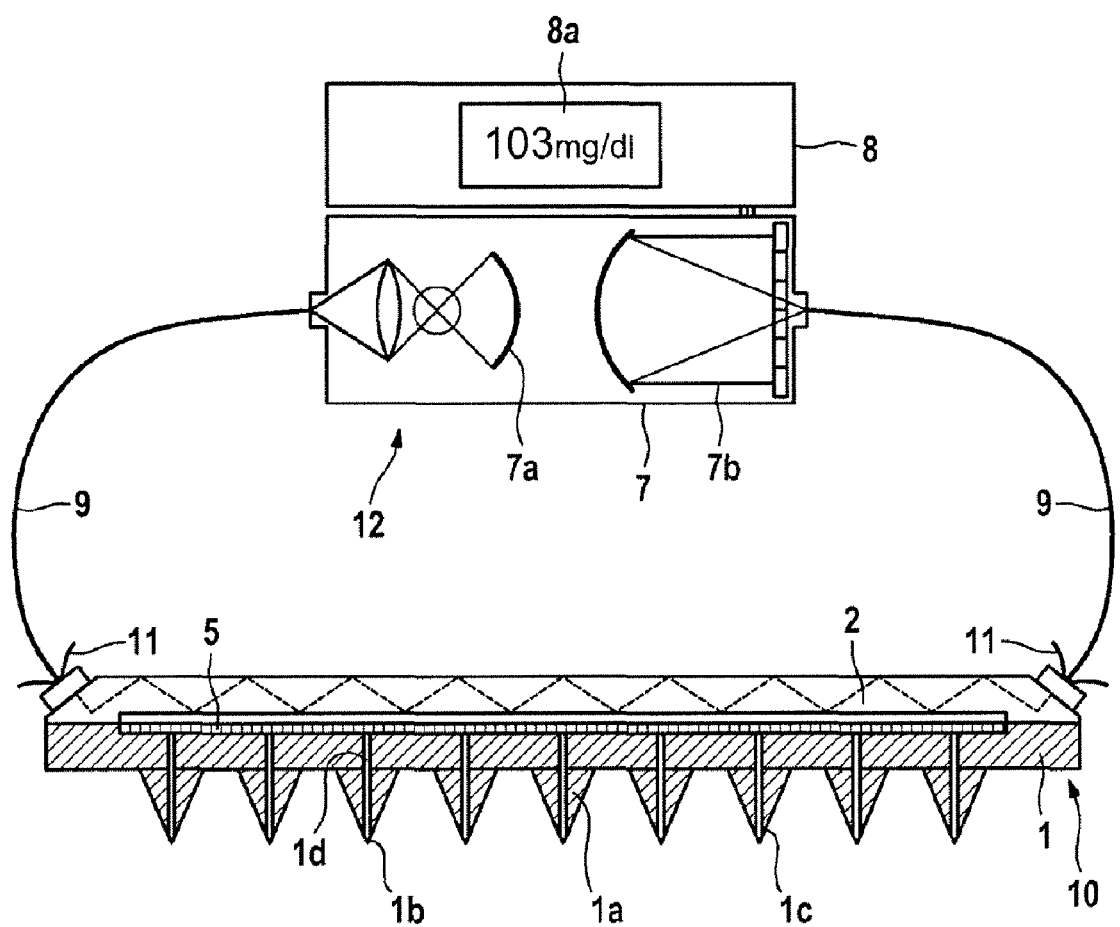
FIG. 4 is a schematic diagram of a system in which the sensor, including the needle array and window, is connected to an optical module which includes a measurement display.
Figure 5A:
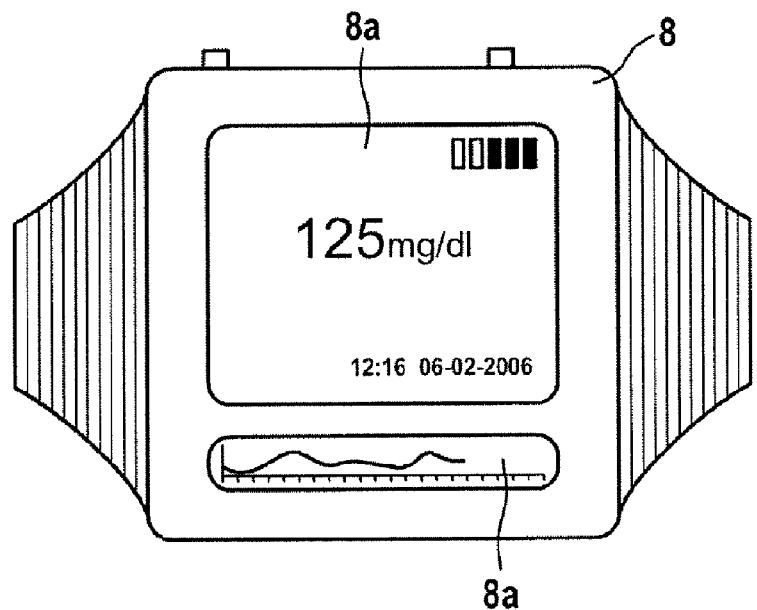
FIG. 5a is a schematic diagram of a watch as a measuring system.
Figure 5B:
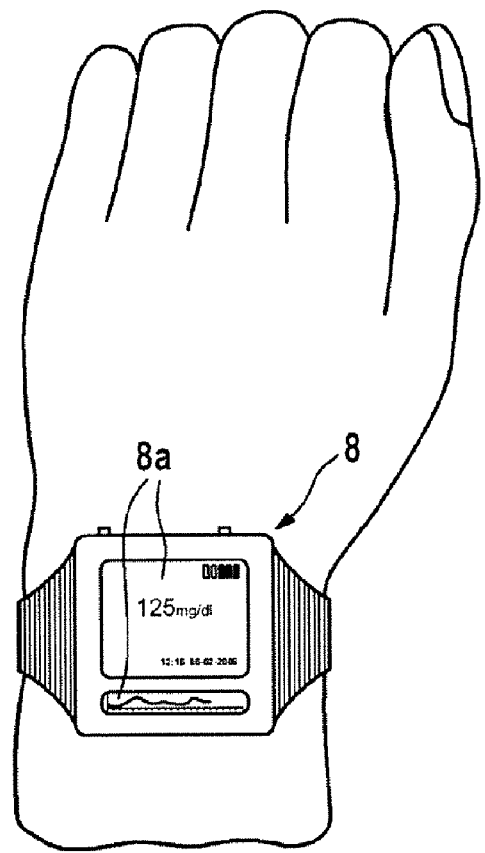
FIG. 5b is a view of the watch of FIG. 5a shown on the wrist of the user.
Figure 5C:
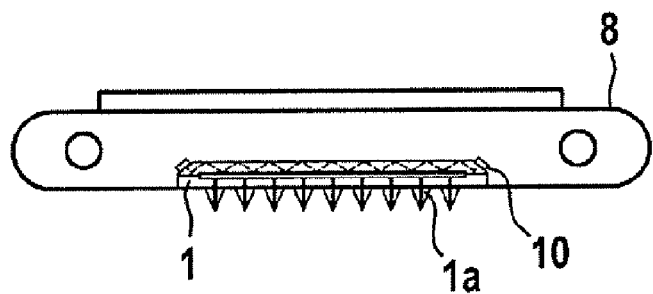
FIG. 5c is a side view of a watch having an integrated needle sensor.
Figure 5D:
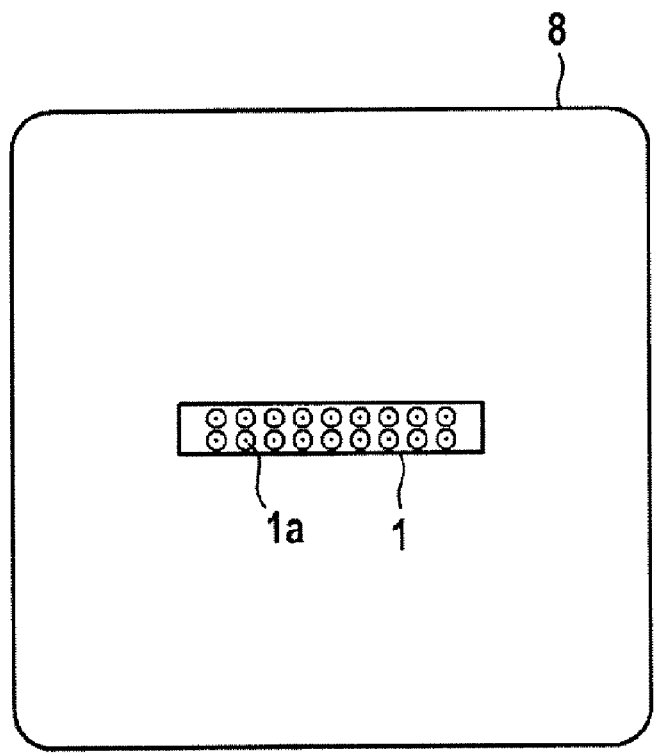
FIG. 5d is a top view of the rearside of a watch having an integrated needle sensor.

A system is shown in FIG. 4 in which the sensor 10 is connected to the optomodule 12. The optomodule 12 consists of the light guides 9 which can be connected to the window 2 by means of a clamping element 11. A light guide 9 is connected to a light source 7a and the other light guide 9 is connected to a detector 7b on the side facing away from the window 2. The light source 7a and the detector 7b are located in a housing 7. The light source 7a and the detector 7b are connected to a control and evaluation module 8 which controls the light source 7a as well as the detector 7b. Another function of the evaluation module 8 is to receive and evaluate the light signals from the detector 7b. After the evaluation the results can be displayed to the patient by means of display 8a.

An exemplary embodiment of the sensor 10 is shown in FIG. 5 in which the needle array together with the window are integrated into an optomodule 8 in the form of a watch. The watch 8 also has a display 8a for the evaluated measurement results as shown in FIGS. 5a and 5b. FIGS. 5a and 5b show a top view of the watch 8 whereas FIG. 5c shows a side view of the watch 8. It can be seen that the sensor 10 including the needle array 1 is situated on the underside of the watch 8. The needles 1a protrude from the underside of the watch 8 such that they can be pressed into the skin of the patient when the watch 8 is worn. FIG. 5d shows a top view of the rear side of the watch 8. The needle array 1 is situated on a part of the rear face of the watch 8.

Figure 6A:
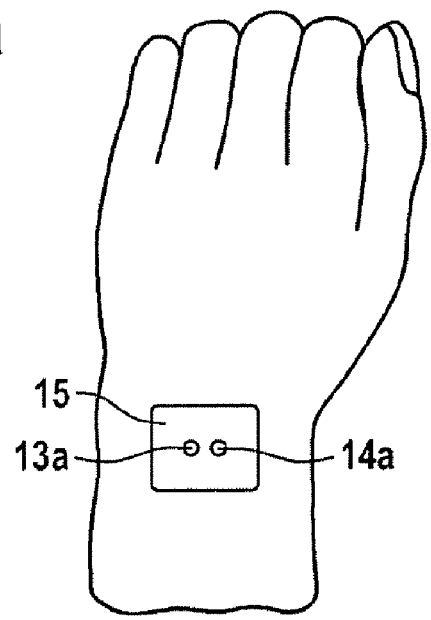
FIG. 6a is a schematic diagram of a plaster (with an integrated needle array) which is applied to the skin and has connections to an optomodule.
Figure 6B:
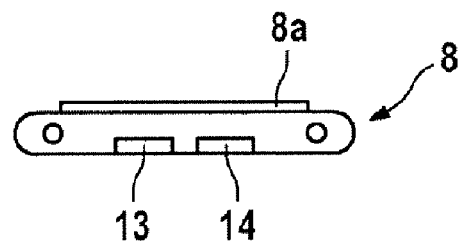
FIG. 6b is a side view of an optomodule shown in the form of a watch having an integrated connection to the sensor.
Figure 6C:
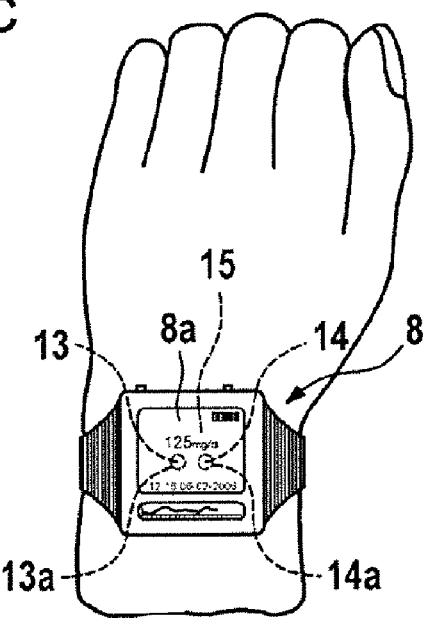
FIG. 6c is a schematic diagram of a system in which the sensor including needle array is integrated into a plaster and is connected to an optical module in the form of a watch.

A plaster 15 is shown in FIG. 6a which is applied to the skin of a patient. The plaster 15 can contain the sensor 10 (not visible here). Two connections 13a and 14a which can be connected either optically or electrically to an optomodule 8 are attached to the side opposite to the skin of the patient. FIG. 6b shows an optomodule 8 in the form of a watch in a side view. The display is situated on the upper side and two connections 13 and 14 are arranged on the underside which serve to connect the optomodule 8 to the plaster 15 and, via the connections 13 and 14, also to the sensor 10. This can either be an optical or electrical connection depending on whether the light source and detector are integrated in the optomodule or in the sensor. The connection of the optomodule 8 to the plaster is shown in FIG. 6c.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A sensor for optical determination of the concentration of an analyte in a body fluid, comprising:
   a needle arrangement including a plurality of needles, each needle having a distal end, a proximal end, and a hollow space extending from the distal end to the proximal end, the distal end being configured for lancing and entry of fluid;
   a chamber into which the proximal end opens and in which the fluid can be collected; and
   a window which is at least partially permeable to infrared radiation and is in contact with the chamber, the chamber forming an interspace between the needle arrangement and the window.

2. The sensor of claim 1, wherein the window is permeable to light of various wavelengths.

3. The sensor of claim 1, wherein the window is permeable to light having a wavelength in the range of 500-20,000 nm.

4. The sensor of claim 3, wherein the window is permeable to light having a wavelength in the range of 2000-12,000 nm.

5. The sensor of claim 1, further comprising a filter located in the needle arrangement and configured for separating molecules of greater than 10 TDa.

6. The sensor of claim 1, wherein the volume of the chamber is 1 to 1000 nl.

7. The sensor of claim 1, wherein the sensor contains no reagent which reacts with the analyte.

8. The sensor of claim 1, further comprising:
   a light source configured to transmit radiation into the window;
   a detector positioned on a side of the window opposite the light source and configured to generate measurement signals; and
   an evaluation unit configured to calculate the concentration of an analyte from the measurement signals.

9. The sensor of claim 8, wherein the light source is configured to irradiate one side of the window and the detector is configured to capture the radiation from the opposite side of the window.

10. The sensor of claim 9, wherein the window is configured to reflect at least a portion of the light which irradiates the window.

11. The sensor of claim 8, wherein at least one of the light source and the detector is connected to the window by an optomodule.

12. The sensor of claim 8, further comprising a membrane filter incorporated into the needle arrangement.

13. A fluid sampling and analyte concentration measurement system, comprising:
   a chamber in which fluid can be collected;
   a plurality of needles, each needle having a distal end, a proximal end, and a hollow space extending therebetween, the distal end being configured for lancing and entry of fluid, the proximal end opening into the chamber;
   a window which is at least partially permeable to infrared radiation positioned adjacent the chamber, the chamber forming an interspace between the needles and the window;
   a light source configured to transmit radiation into the window;
   a detector positioned on a different side of the window than the light source and configured to generate absorption measurement signals; and
   an evaluation unit coupled to the detector and configured to calculate the concentration of an analyte in the fluid from the absorption measurement signals.

14. The system of claim 13, further comprising a filter disposed between the proximal end of the needles and the chamber, wherein the filter is configured to prevent molecules of greater than 10 TDa from entering the chamber.

15. The system of claim 13, wherein the chamber has a volume of 1 to 1000 nl.

16. The system of claim 13, wherein the window is permeable to light having a wavelength in the range of 500-20,000 nm.

17. The system of claim 16, wherein the window is permeable to light having a wavelength in the range of 2000-12,000 nm.

18. The system of claim 13, wherein the needles are arranged in an array.

19. The system of claim 18, wherein the window extends over substantially the entire length of the array.

20. The system of claim 19, wherein the window has a thickness in the range of about 0.025 to 0.2 mm.

21. The system of claim 20, wherein the array comprises a two-dimensional matrix.

22. The system of claim 13, wherein the window is configured for attenuated total reflection.

23. A method of determining concentration of analyte in a body fluid sample of a patient, comprising:
   inserting distal ends of a plurality of needles into the patient's skin and drawing body fluid into the needles, the needles being coupled to a chamber with a proximal end of each needle being in fluid communication with the chamber;
   transferring the body fluid from the needle into the chamber, the chamber being positioned adjacent a window and forming an interspace between the needles and the window, and wherein the body fluid contacts the window;
   directing light through the window;
   detecting the light that passes through the window; and
   determining analyte concentration from the detected light.

24. The method of claim 23, wherein the light is totally reflected several times at internal surfaces of the window before the step of detecting the light, whereby the method comprises attenuated total reflectance.

25. The method of claim 23, wherein the needles are arranged in an array.

26. The method of claim 23, wherein the directed light has a wavelength in the range of 2000 to 12,000 nm.

27. The method of claim 23, wherein the determining analyte concentration comprises continuous measurement.

28. The method of claim 27, further comprising continuously displaying the analyte concentration.

29. The method of claim 23, wherein the determining analyte concentration comprises a single measurement.

30. The method of claim 23, wherein the light comprises infrared light.

31. The method of claim 23, further comprising arranging a filter between the proximal end of the needles and the chamber and filtering high molecular weight constituents from the body fluid sample.

32. The method of claim 23, wherein the step of drawing the body fluid sample into the needles use capillary action.

33. The method of claim 23, further comprising arranging the needles, window and chamber in the form of a system and applying the system to the skin of a patient with an adhesive.

34. The method of claim 33, further comprising integrating the system into a plaster adhesive.

35. The method of claim 23, wherein the analyte concentration is determined from infrared absorption measurement, whereby reagents to react with the body fluid sample are unnecessary.

36. The method of claim 23, wherein the analyte is glucose.

37. The method of claim 23, wherein the body fluid comprises interstitial fluid.

38. The method of claim 23, further comprising providing an optomodule having a light source and a detector and coupling the optomodule to the window.

39. The method of claim 23, wherein the light directed through the window comprises monochromatic light.

40. The method of claim 23, wherein the analyte comprises one or more of glucose, creatinine, triglycerides, urea and cholesterol.

41. The method of claim 23, wherein the chamber has a volume of between 1 and 1000 nl.

42. A sensor for determining the concentration of an analyte in a body fluid, comprising:
   a chamber in which fluid can be collected;
   a plurality of needles, each needle having a distal end, a proximal end, and a hollow space extending therebetween, the distal end being configured for lancing and entry of body fluid, the proximal end opening into the chamber;
   a window positioned adjacent the chamber and having a surface configured to contact body fluid collected in the chamber, the chamber forming an interspace between the needles and the window, the window configured for receiving radiation, reflecting the radiation from interior surfaces of the window, and transmitting the radiation from the window.

43. The sensor of claim 42, further comprising a light source positioned on one side of the window, a detector positioned on a different side of the window than the light source, and an evaluation unit coupled to the detector and configured to calculate the concentration of an analyte in the body fluid.

44. The sensor of claim 42, further comprising a filter disposed between the proximal end of the needles and the chamber, wherein the filter is configured to prevent molecules of greater than 10 TDa from entering the chamber.

45. The sensor of claim 42, wherein the chamber has a volume of 1 to 1000 nl.

46. The sensor of claim 42, wherein the window is permeable to light having a wavelength in the range of 2000-12,000 nm.

47. The sensor of claim 42, wherein the needles are arranged in an array.

48. The sensor of claim 47, wherein the window extends over substantially the entire length of the array.

49. The sensor of claim 47, wherein the window has a thickness in the range of about 0.025 to 0.2 mm.

50. The sensor of claim 42, further comprising an optomodule detachably mountable thereto, the optomodule comprising a light source configured to transmit radiation into the window, a detector configured to detect radiation that passes through the window, and an evaluation unit configured to calculate the concentration of an analyte in the body fluid.

* * * * *